US006610266B2

(12) United States Patent
Withiam et al.

(10) Patent No.: US 6,610,266 B2
(45) Date of Patent: Aug. 26, 2003

(54) CALCIUM METASILICATES AND METHODS FOR MAKING

(76) Inventors: Michael C. Withiam, 25 Ketcham Ct., Landenberg, PA (US) 19350; Donald P. Conley, 73 Groff Farm La., Conowingo, MD (US) 21918; Edward T. Yannul, 61 Steelman Dr., Conowingo, MD (US) 21918

( * ) Notice: Subject to any disclaimer, the term of this patent is extended or adjusted under 35 U.S.C. 154(b) by 0 days.

(21) Appl. No.: 10/156,890

(22) Filed: May 29, 2002

(65) Prior Publication Data

US 2003/0138369 A1 Jul. 24, 2003

Related U.S. Application Data

(60) Provisional application No. 60/333,899, filed on Nov. 28, 2001.

(51) Int. Cl.⁷ ............................ C01B 33/26; A61K 9/14; A61K 9/20; A61K 7/00
(52) U.S. Cl. ................. 423/331; 501/154; 424/400; 424/401; 424/438; 424/439; 424/464; 424/489; 424/600
(58) Field of Search ................. 424/489, 401, 424/438, 439, 400, 600, 682, 464; 423/331; 501/154; 106/470

(56) References Cited

U.S. PATENT DOCUMENTS

| | | | | | |
|---|---|---|---|---|---|
| 3,966,884 | A | * | 6/1976 | Jacob | 423/331 |
| 3,967,974 | A | * | 7/1976 | Ohnemuller et al. | 106/470 |
| 5,032,552 | A | * | 7/1991 | Nonami et al. | 501/95.3 |
| 5,393,472 | A | * | 2/1995 | Shaw | 264/660 |
| 5,424,351 | A | * | 6/1995 | Komatsu et al. | 524/424 |
| 5,994,348 | A | | 11/1999 | Ku et al. | |
| 6,103,007 | A | * | 8/2000 | Wu et al. | 106/690 |
| 6,133,378 | A | * | 10/2000 | Davis et al. | 525/240 |

FOREIGN PATENT DOCUMENTS

| | | |
|---|---|---|
| EP | 1 145 711 | 10/2001 |
| JP | H10-114655 | 5/1998 |
| WO | WO 95/03785 | 2/1995 |
| WO | WO 99/32092 | 7/1999 |

* cited by examiner

Primary Examiner—David Sample
(74) Attorney, Agent, or Firm—Carlos Nieves; David Mitchell Goodrich

(57) ABSTRACT

Disclosed is calcium metasilicate having an aspect ratio (average major axial diameter/average minor axial diameter) of from about 1:1 to about 2.5:1, and an oil absorption of from about 20 ml/100 g to about 220 ml/100.

28 Claims, 2 Drawing Sheets

CALCIUM METASILICATES AND METHODS FOR MAKING this application claims the benefit of provisional application No. 60/333,899 filed Nov. 28, 2001.

BACKGROUND OF THE INVENTION

Many consumer products, such as health and personal care products, are manufactured and packaged in solid, compacted form. The solid, compacted product form has several advantages over other product forms, such as relative ease of manufactures and durability in shipment and convenience in storing for retailers and consumers alike. The tablet solid form is particularly well-suited for over-the-counter prescription pharmaceutical, and nutritional products that are to be administered orally, because virtually any pharmaceutically-active medicament is capable of being granulated and prepared in powdered form without affecting its medicinal effectiveness. Moreover, after being swallowed, the tablets quickly disintegrate within the acidic environment of the stomach, and the active medicament within the tablet is readily digested and absorbed into the blood stream.

However, in certain situations it would be beneficial if the tablet would disintegrate in the mouth so that the active pharmaceutical could be delivered to the blood stream of a patient without the necessity of swallowing the tablet. For example, children and advanced geriatric patients (those over 80 years old) often have difficulty swallowing pills, and a tablet that dissolves or rapidly disintegrates in the mouth would provide a convenient and effective solid form delivery system for such patients. Additionally, a tablet that dissolves, or disintegrates, in the mouth would be helpful for mentally disabled individuals who require treatment with pharmaceuticals, but refuse to swallow tablets.

Yet another situation where oral disintegration would be helpful is where water may not be readily available to assist in swallowing the tablet, such as when a person is traveling in an automobile or under certain working conditions.

Unfortunately, most tablets do not readily dissolve in the mouth, but instead disintegrate in a slow and uneven fashion, so that if the tablet is not swallowed, then a dosage significantly below the therapeutically effective level will be delivered to the bloodstream. This is particularly serious when a pharmaceutical tablet is administered to treat a bacterial disease, and the refusal of a patient to swallow the tablet results in a sub-therapeutically effective amount of an antibiotic being delivered to the bloodstream, allowing the bacteria to develop resistance to the antibiotic. Given the forgoing there is a continuing need for solid form pharmaceutical preparations that rapidly disintegrate. Particularly needed are tablet compositions that readily disintegrate in the mouth, and thereby eliminate the need for the tablet to be swallowed.

BRIEF SUMMARY OF THE INVENTION

The present invention includes a calcium metasilicate having an aspect ratio (average major axial diameter/average minor axial diameter) of from about 1:1 to about 2.5:1, and an oil absorption of from about 20 ml/100 g to about 220 ml/100 g.

The invention also includes a method of forming a dehydrated calcium metasilicate comprising the steps of: providing a calcium source and a silica source, at a molar ratio of calcium in the calcium source to silica in the silica source is from about 0.75 to about 1.3, preferably from about 0.95 to about 1.05; mixing the calcium source with the silica source to form a homogeneous mixture; and heating the homogenous mixture to form dehydrated calcium metasilicate.

The invention also includes pharmaceutical, food, agricultural and cosmetic products including the calcium metasilicate prepared according to the present invention.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
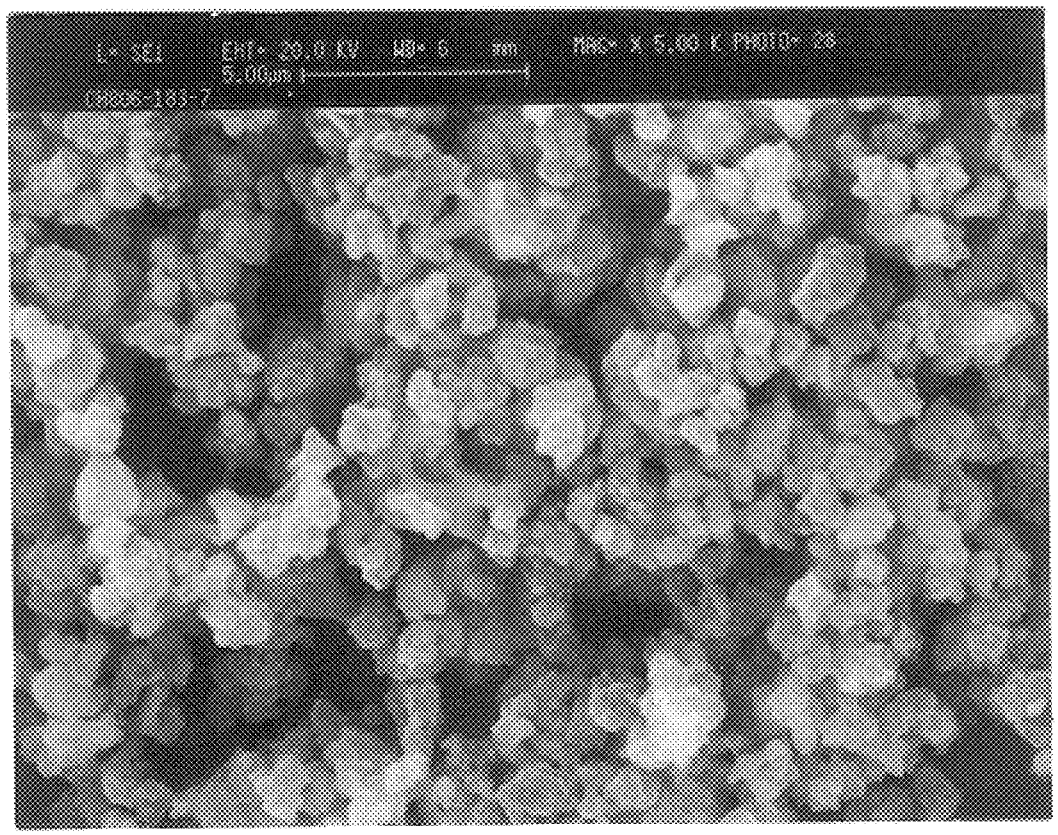
FIG. 1 is an SEM Micrograph of the calcium metasilicate material prepared in Example 4, below.

All parts, percentages and ratios used herein are expressed by weight unless otherwise specified. All documents cited herein are incorporated by reference.

By "mixture" it is meant any combination of two or more substances, in the form of, for example without intending to be limiting, a heterogeneous mixture, a suspension, a solution, a sol, a gel, a dispersion, or an emulsion.

The present application relates to synthetic calcium metasilicate useful as an additive in pharmaceutical, food, agricultural, personal care, home care and like products, which when incorporated in a solid, formed product (e.g., a tablet) significantly increases the disintegration rate of the formed product, when contacted by a substantially aqueous environment (such as mammalian saliva or mucous). While not wishing to be limited by theory, it is believed that calcium metasilicates prepared according to the present invention provide this enhanced disintegration performance because of their high oil absorption and low aspect ratio. In particular, the high oil absorption indicates that the calcium metasilicates absorb high amounts of water, while the low aspect ratio means that the calcium metasilicates form an interlocking structure with a high intraparticle void volume. Thus, water is absorbed by the calcium metasilicates and penetrates into the particle voids to push apart the particles of the solid product. The present calcium metasilicates are particularly effective at enhancing the rate of disintegration of tablet compositions that contain one or more disintegrants, because as the calcium metasilicate provides the initial separation and untangling of adjoining particles, the disintegrants then provide a more substantial disintegrating effect to the separated particles.

The present calcium metasilicates are particularly suitable for pharmaceutical product preparations prepared in solid form and meant to be orally administered. When included in such products, the tablet readily disintegrates in the mouth, and thus eliminates the need for swallowing. Also, these calcium metasilicates are useful not only in tablets meant for human consumption, but may also be particularly useful in veterinary pharmaceuticals for pets as many pets have acquired the reputation of being somewhat reluctant to swallow solid formed pharmaceutical preparations.

Additionally, these calcium metasilicates are useful in products which may be in forms other than tablets, such as certain solid formed food products, such as bouillon cubes, yeast cakes and the like; agricultural products such as herbicides, fungicides, pesticides, and fertilizers; and personal and home care products such as bath granules, fragrance, soap, and shampoo products for camping or boating, where carrying aqueous solutions is inconvenient, and automatic dishwashing detergent, laundry detergent, toilet bowl cleaners and the like.

Calcium metasilicates prepared according to the present invention, as well as methods for making them, will now be discussed in detail. Then products incorporating these ingredients, particularly solid, formed pharmaceutical preparations will be discussed and examples of such products provided.

Calcium metasilicate ($CaSiO_3$) is used to describe materials that are characterized by a ratio of moles of calcium to mole of silicon, of about 1.0. Naturally occurring mineral forms of the material range from about 0.8 to 1.3 $CaO/SiO_2$ molar ratio. More commonly, and specifically, the term calcium metasilicate is used to describe the various types of minerals and synthetic (amorphous and crystalline) materials chemically-resembling wollastonite. It is accepted that wollastonite minerals occur in three crystalline types, type 1A, 2M and 7M, but type 1A is the only prevalent form of wollastonite with types 2M, and 7M being very rare, and typically not naturally occurring in nature. Details of types 1A, 2M, and 7M are given below in table 1.

TABLE I

Common Species of Calcium Metasilicate

| Species | Common name | Crystal species | Occurrence |
| --- | --- | --- | --- |
| 1A | Wollastonite | Triclinic | Common |
| 2M | Parawollastonite | Monoclinic | Very rare |
| 7M | Pseudowollastonite | Triclinic | Very rare |

Naturally-occurring calcium metasilicate is mined at many different sites throughout the world. After being mined, the calcium metasilicate is beneficiated to yield various grades, and depending on its specific grade, used in a variety of industrial applications such as rheology modifiers and structural additives. These naturally-occurring calcium metasilicates have a crystalline form and high aspect ratios (above 3:1, and in some case above even above 20:1), that provides rigidity and strength. Properties of commonly available naturally-occurring mined wollastonite are given in Table II below.

TABLE II

Properties of Mined, Naturally-occurring, Commercially Available Wollastonite.

| Wollastonite Product | Density, g/cc | Crystal Morphology | Crystal Aspect ratio | Oil Absorption, ml/100 g | Brightness % |
| --- | --- | --- | --- | --- | --- |
| VANSIL W10 | 0.29 | acicular | >3:1 | 19 | 80 |
| Reade 400 Powder | 0.39 | acicular | >3:1 | 45 | 89 |
| Boud Grade 2RF | 0.37 | acicular | 20:1 | 40 | 65 |
| Boud Grade W4 | 0.77 | — | 3:1 | 28 | 75 |

In addition to the naturally occurring calcium metasilicates, calcium metasilicates may also be produced synthetically for use in specialty ceramics and materials research. However, this calcium metasilicates are not crystalline, but rather have a glassy or amorphous microstructure. Moreover, the poor oil absorption performance of synthetic calcium metasilicates, which have about half the oil absorption capacity as naturally occurring calcium metasilicates (shown in Table III, below), indicates that synthetic calcium metasilicates have a rather low intraparticle void volume.

TABLE III

Physical properties of synthetically produced calcium metasilicates.

| calcium silicate | Morphology | Oil Absorption, cc/100 g | Surface Area BET, $m^2/g$ | Brightness, % |
| --- | --- | --- | --- | --- |
| Aldrich | Amorphous, Glassy irregular | 8 | 2 | 84 |
| CERAC | Mixed glassy and porous irregular | 10 | 2 | 85 |

In contrast to either the naturally-occurring or synthetic calcium metasilicates discussed above, the inventive calcium metasilicates disclosed in the present application have a low aspect ratio, and form structured aggregates of uniform particles yielding high oil or water absorption characteristics. Specifically, this low aspect ratio (average major axial diameter/average minor axial diameter) of the calcium metasilicate is between about 1:1 to about 2.5:1, preferably from about 1:1 to about 1.5:1, and an oil absorption of from about 20 ml/100 g to about 220 ml/100 g, preferably from about 20 ml/100 g to about 100 ml/100 g. (The techniques for measuring aspect ratio and oil absorption are discussed in greater detail below. The major axis is perpendicular, although not necessarily coplanar, with the minor axis.) Preferably the calcium metasilicate is dehydrated (or "calcined"). The silica source can be selected from naturally occurring pure forms of crystalline silicon dioxide or from synthetic amorphous silicon dioxide. The preferred form of silica is amorphous silicon dioxide, such as precipitated silica, silica gel, fumed silica or colloidal silica as described in USP/NF Monographs entitled, "Dental-Type Silica, Silicon Dioxide and Colloidal Silicon Dioxide." The calcium source may be selected from the group including, silicates, oxides, carbonates, sulfates, hydroxides and salts or mixtures thereof. The preferred source of calcium is calcium hydroxide.

When mixed together, the $CaO/SiO_2$ ratio is between about 0.75 and 1.3, preferably between about 0.95 and 1.05. By the present invention, it has been discovered that by maintaining the $CaO/SiO_2$ mole ratio during mixing in the proximity of about 1:1 (such as in the aforementioned ranges), crystalline silica formation is prevented during subsequent high-temperature dehydration.

Mixing of the silica and calcium should continue until a homogeneous mixture is formed. Preferably the calcium and silica are combined with sufficient water to provide an easily mixed suspension of the materials.

Once a homogenous mixture is obtained, it can be dried to remove any excess water. Then the mixed solids-homogenous mixture (either dried or undried) is dehydrated (or "calcined") at temperatures of between about 600° C. and about 1200° C., preferably 700° C. to 900° C., for a time period of between 10 and 120 minutes, preferably between about 10 to 60 minutes.

In an especially preferred embodiment of the present invention, milk of lime slurry is combined with a suspension of amorphous silica in a well-agitated vessel to yield homogeneous mixed solids having a $CaO/SiO_2$ molar ratio between 0.95 and 1.05. The homogenous mixed solids are removed from the vessel and dried in an atomizing spray dryer to obtain a powder in which a substantial portion of the particulates have a size less than 300 µm. The particulates are then calcined in an indirect heated fluid bed calciner at 800° C. for 10 to 60 minutes, preferably 10–30 minutes, and recovered as fine particle wollastonite aggregates. The recovered particulates may optionally be comminuted to finer particle sizes, by any conventional means.

The present calcium metasilicates are included in solid, formed pharmaceutical preparations along with one or more pharmaceutically active ingredients. Suitable pharmaceutically active ingredients include nourishing and health-promoting agents, antipyretic, analgesic, anti-inflammatory agents, antipsychotic drugs, antianxiety drugs, antidepressants, hypnotic-sedatives, spasmolytics, central nervous system affecting drugs, cerebral metabolism ameliolators, antiepileptics, sympathomimetic agents, gastrointestinal function conditioning agents, antacids, antiulcer agents, antitussive-expectorants, antiemetics, respiratory stimulants, bronchodilators, antiallergic agents, dental buccal drugs, antihistamines, cardiotonics, antiarrhythmic agents, diuretics, hypotensive agents, vasoconstrictors, coronary vasodilators, peripheral vasodilators, antihyperlipidemic agents, cholagogues, antibiotics, chemotherapeutic agents, antidiabetic agents, drugs for osteoporosis, skeletal muscle relaxants, antidinics, hormones, alkaloid narcotics, sulfa drugs, antipodagrics, anticoagulants, anti-malignant tumor agents, agents for Alzheimer's disease, etc. These calcium metasilicates may also be included in veterinary pharmaceutical preparations.

These solid formed pharmaceutical preparations may also include one or more disintegration aids. Preferably the disintegration aid acts by swelling or wicking in of water. Suitable disintegrants include natural, modified or pregelatinized starch; natural or chemically-modified cellulose, especially crosslinked sodium carboxymethyl cellulose (croscarmellose sodium); gum, especially agar gum, and guar gum; alginic acid or salts thereof; acetates and citrates; sugars (especially lactose, mannitol and sorbitol); aluminum oxide; synthetic polymers such as crospovidone, as well as effervescent disintegrating systems.

As discussed above, the present calcium metasilicates may be used in a variety of different solid, formed pharmaceutical products, especially the tablet form. Tablets are prepared by combining the above ingredients, present at different concentration levels, in a homogeneous mixture. The tablets are then manufactured by using a tableting compacting process. A standard single stroke or a rotary press may be used. The tablets prepared according to this invention may be of any shape, such as round or caplet-shaped, and of any size suitable for human or animal use.

The calcium metasilicates disclosed in the present application may also be used in other personal care, home care, agricultural and food products.

The invention will now be described in more detail with respect to the following, specific, non-limiting examples.

EXAMPLE 1

Calcium metasilicate was prepared according to conventional, prior art methods by mixing 10 g of Hubersorb® 250 amorphous calcium silicate, commercially available from J. M. Huber Corporation, Havre de Grace, Md., with 5.4 g of dry calcium hydroxide powder (Chemstone Corporation, Strasburg, Va.) in a V-blender for 15 minutes. Then this mixture was dehydrated (or "calcined") in an autoclave at 900° C. for 4 hours. The final dehydrated product was recovered and its composition determined using powder x-ray diffraction to be calcium metasilicate, primarily in the wollastonite form with small amounts of crystalline silica (the cristobalite polymorph) present (see Table V, below). The properties of the Example 1 calcium metasilicate are shown in Table IV, below.

EXAMPLE 2

In a first step of this example, amorphous silica suitable for use in the production of calcium metasilicate was prepared by adding sulfuric acid to a dilute waterglass solution in a well-agitated mixing vessel to affect the precipitation of amorphous hydrated silica. Specifically, a total of 278 gallons of sulfuric acid at a concentration of 11.5% is added at a rate of 4.7 gpm to 500 gallons of waterglass solution (3.3 $SiO_2/Na_2O$ mole ratio) containing 13% sodium silicate solids while mixing at a temperature of 95° C. The addition of the sulfuric acid was continued until a pH of 5.5 was obtained, and the reaction mixture was digested for 1 hr. The resulting suspension of silica particles was recovered by filtration, and washed and dried to form a finely divided reactive silica powder.

Then, 90 kg of an aqueous solution of this reactive silica powder prepared above (16% solids) was mixed with 105 Kg of lime slurry (18% solids) in an agitated vessel until a homogenous mixed solids suspension was obtained. This suspension was digested for 2 hours at 95° C., and the suspended solids recovered and dried in a forced air oven at 150° C. to a moisture level below 5%. The dried amorphous calcium silicate hydrate was dehydrated at 900° C. in a kiln for 1 hour. Highly structured wollastonite was formed. X-ray diffraction, analysis see Table IV, did not indicate the presence of phases of other polymorphs of calcium metasilicate nor any crystalline silica. The properties of the calcium metasilicate prepared in Example 2 are shown in Table IV, below.

TABLE IV

Physical Properties of Calcium Metasilicate Prepared in Examples 1 and 2

| | Ratio of $CaO/SiO_2$ | XRD Phase A | XRD Phase B | Crystal Aspect ratio | Oil Absorption ml/100 g |
|---|---|---|---|---|---|
| Example 1 | 0.67 | Wollastonite 2M | cristobalite | 1:1 | 80 |
| Example 2 | 1.01 | Wollastonite 2M | none | 1:1 | 32 |

The oil absorption shown in Table V (and throughout this application) is measured with the rubout method. In this test, oil is mixed with a powdered sample and rubbed with a spatula on a smooth surface until a stiff putty-like paste is formed. By measuring the quantity of oil required to have a paste mixture, which will curl when spread out, one can calculate the oil absorption value of the metasilicate, the value which represents the volume of oil required per unit weight of metasilicate to completely saturate the metasilicate absorptive capacity. Calculation of the oil absorption value was done according to equation (I):

$$\text{Oil absorption} = \frac{\text{ml oil absorbed}}{\text{weight of sample, grams}} \times 100 \quad \text{(I)}$$

$$= \text{ml oil}/100 \text{ grams sample}$$

Figure 2:
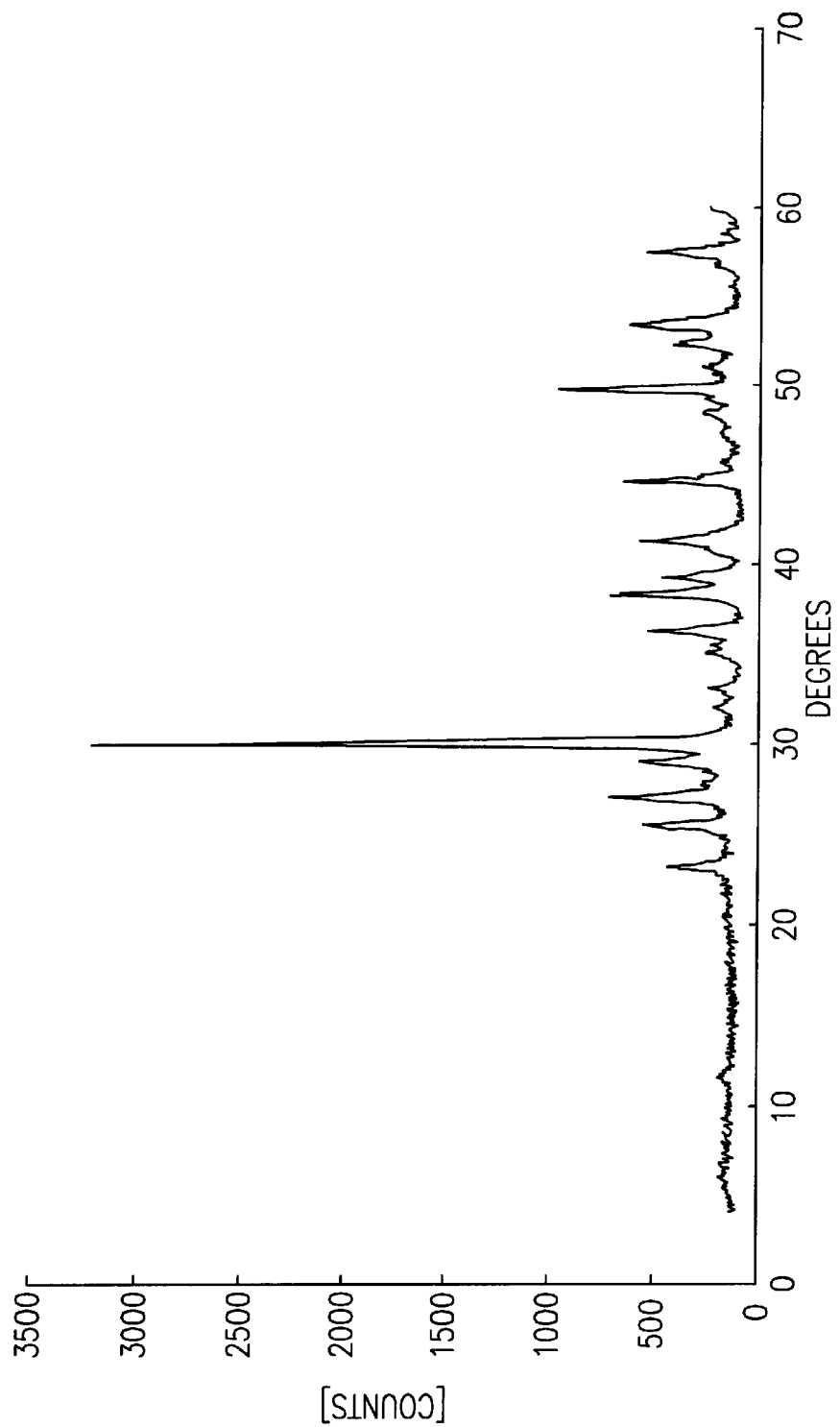
FIG. 2 is an X-ray diffraction pattern of the calcium metasilicate prepared in Example 4, below.

The aspect ratio given in Table IV is the average major axial diameter/average minor axial diameter, and can be measured as follows. First, samples of the calcium metasilicate material are ground to obtain separate individual particles. This material is dispersed in isopropanol to allow preparation of specimens with unagglomerated individual particles. The specimen is carbon coated before being imaged using standard Scanning Electron Microscopy. SEM micrographs are made at a magnification of 1000× on 77 mm×114 mm images digitized using either a direct digital image capture or through the use of a flat bed scanner. The digital micrographs are evaluated using ImagePro Plus 3.0 software. Images are converted to 2 color high contrast digital images using a threshold pixel gray value of 140. An individual pixel in an image is approximately 0.162 microns in width and height. The calcium metasilicate particle aspect ratio is measured using image analysis to calculate particle width and particle length using the particle information. A histogram of aspect ratio allows the prominent aspect ratio to be determined. A minimum of 100 measurements are made, to assure statistical significance.

powder was then calcined in an indirect gas fired fluid bed calciner for 30 minutes at 800° C. The recovered fine particle size calcium metasilicate was analyzed by powder x-ray diffraction. A θ/2θ type diffractometer equipped with a x-ray tube having a copper anode was used. The diffraction scan obtained from this analysis is shown in FIG. 2. This scan indicates the presence of wollastonite 2M, with no traces of crystalline silica. Properties of Example 4 calcium metasilicate are given in Table V, below.

EXAMPLE 5

In this example, synthetic calcium metasilicate was produced according to Example 4, except that the recovered dry powder was calcined for 1 hour at 700° C. The calcined recovered material was characterized by x-ray powder diffraction as dehydrated amorphous calcium metasilicate. Properties of Example 5 calcium metasilicate are given in Table V below.

TABLE V

Physical and Crystallographic Properties of Calcium Metasilicate Prepared in Examples 3–5

| Product | Density g/cc | Morphology | $CaO/SiO_2$ Molar ratio | Aspect ratio | Oil Absorption ml/100 g | Surface Area BET, $m^2/g$ | Brightness % |
| --- | --- | --- | --- | --- | --- | --- | --- |
| Example 3 | 0.37 | Wollastonite 2M monoclinic | 0.81 | 1:1 | 22 | 1 | — |
| Example 4 | 0.39 | Wollastonite 2M monoclinic | 0.85 | 1:1 | 70 | 6 | 86 |
| Example 5 | 0.13 | Structured, spheroidal Amorphous | 0.85 | ~1:1 | 203 | 86 | 90 |

EXAMPLE 3

Calcium metasilicate was prepared according to the present invention by mixing 10.5 g of a pure dry $Ca(OH)_2$ (from Chemstone Corporation) with 56.25 g of aqueous slurry of the reactive silica slurry prepared in Example 2 (with 16% solids) to achieve a homogenous mixture. The mixture was thereafter filtered to recover the solids and then dried at 105° C. for 16 hours, and then dehydrated (calcined) at 900° C. in a kiln for 1 hour. The recovered product was characterized by x-ray powder diffraction as wollastonite 2M with no traces of crystalline silica. Properties of Example 3 calcium metasilicate are given in Table V below.

EXAMPLE 4

A commercial scale embodiment of the process for preparing calcium metasilicate according to the present invention is as follows. First, 4688 pounds (approximately 2131 kg) of the slurry of reactive silica prepared in Example 2 (with 15.2% solids) was added to a stirred vessel at 40° C. Then, 424 gallons (approximately 1611 liters) of milk of lime slurry (with 20% solids) was added at a rate of 25 gallons per minute (approximately 95 liters per minute). Mixing was continued for 20 minutes, to attain an intimately mixed homogenous suspension. This suspension was dewatered using a rotary vacuum filtration device and dried in an atomizing spray drier. The recovered fine particle size dried All of the calcium metasilicates prepared according to examples 3–5 have a structured, spheroidal shape, a $CaO/SiO_2$ mole ratio of about 0.85 and contain no crystalline silica. Examples 3 and 4 calcium metasilicates were calcined at 900° C. and 800° C., respectively, both yielding Wollastonite 2M with a monoclinic crystal structure, while example 5, calcined at 700° C., remained amorphous, albeit dehydrated. The unique aggregated spheroidal structure of the calcium metasilicate prepared according to the present invention results in a material structure having higher intraparticle void volume as indicated by high oil absorption. The BET surface area in Table V was determined by the BET nitrogen absorption method of Brunaur et al., as reported in the J. Am. Chem. Soc. 60, 309 (1938).

The brightness of the powder samples prepared in Examples 3–5 was measured using a Technidyne Brightmeter S-5/BC according to TAPPI test methods T452 and T646, and ASTM Standard D985. The Technidyne Brightmeter has a dual beam optical system where the sample is illuminated at an angle of 45°, and the reflected light viewed at 0°. The powdered materials are pressed to about a 1 cm thick pellet with enough pressure to give a pellet surface that is smooth and flat and without loose particles or gloss.

EXAMPLES 6–7

In Example 6, material produced according to Example 4 was roller compacted at 15 bar roll pressure to produce a fine free flowing granular material with improved flowability and having an average size of approximately 300 μm with a density of 0.34 g/cc. In Example 7, the material produced according to Example 5 was roller compacted as taught in Example 6 to an average size of approximately 300 μm with a density of 0.34 g/cc.

EXAMPLE 8

To demonstrate the usefulness in solid compacted pharmaceutical preparations of the calcium metasilicate prepared according the invention, the calcium metasilicate was added to pharmaceutical preparations, the preparations formed into tablets, and the functional properties of the tablets measured. The functional properties of the tablets containing the calcium metasilicates prepared according to the present invention were compared to the functional properties of tablets containing a common excipient such as dicalcium phosphate dihydrate (also known as "DCP"). The DCP was Emcompress X14CX available from Mendell-Penwest Company, Patterson, N.Y. Three different tablet compositions were prepared, with one tablet composition containing no calcium metasilicate serving as a control, while in the other two tablet compositions, the calcium silicate as prepared in Example 3 was substituted for the dicalcium phosphate at levels of 5 wt % and 20% wt %. The exact compositions of the tablets are set forth below in Table VI. (The differences in actual tablet weights reflect differences in the bulk densities of the blends.)

In preparing tablet compositions 2 and 3, the Emcompress DCP was blended with the calcium metasilicate of the present invention until the mixture was homogenous. Then magnesium stearate was added and blending was continued for an additional 3 minutes. The resulting powder was compacted into tablets at two different compaction forces, 7.5 kN and 12 kN on a Stokes B-2 16-station rotary press instrumented to measure compression and ejection forces.

TABLE VI

Tablet Compositions

|  | Tablet 1 | Tablet 2 | Tablet 3 |
|---|---|---|---|
| Calcium metasilicate (from Example 3) | 0% | 5% | 20% |
| Dicalcium phosphate (Emcompress) | 99% | 94% | 79% |
| Magnesium stearate | 1% | 1% | 1% |
| Average tablet weight, mg | 700 | 540 | 460 |

After being made in the manner described above, the hardness and ejection force of the tablets was measured. Tablet hardness (or "crushing strength", these two terms being used interchangeably) is expressed as load required to crush a tablet on end and is measured using a tablet hardness tester, such as a SCHLEUNIGER® Pharmatron tablet hardness tester available from Dr. Schleuniger Pharmatron AG, Solothum, Germany. Generally, the larger the tablet, the higher the hardness. Smaller tablets (¼" round) usually have a hardness of less than about 5 kPa, while larger tablets usually have a hardness of less than about 20 kPa.

Ejection force refers to the force required to free a compressed tablet from within the die used to form the tablet. Ejection force is relevant to high speed compression tableting, accordingly it is desired to keep the ejection force low so as to maintain the compression tableting at high speeds. It is related to the frictional forces developed in the die and the surface of the die's wall with the material being compressed. The tablet ejection forces expressed herein in kg are measured by the use of load cells on the tableting press. A plot is generated which shows the tablet initially breaking away from the die walls followed by a period of sliding, where the friction between the die wall and the tablet is being measured and finally showing the tablet emergence from the die and separation from the die punch face.

For each of the individual tablet compositions 1–3, ten tablets were pressed. The properties set forth in Table VII, below, represent an average of the properties measured for each of the ten tablets.

TABLE VII

Functional Tablet Properties

|  | 7.5 KN Compression Force | | 12 KN Compression Force | |
|---|---|---|---|---|
|  | Hardness (kPa) | Ejection Force (kg) | Hardness (kPa) | Ejection Force (kg) |
| Tablet 1 | 4.6 | 3.3 | 6.5 | 6.6 |
| Tablet 2 | 3.3 | 5.7 | 5.5 | 7.6 |
| Tablet 3 | 3.8 | 6.6 | 6.1 | 8.5 |

As can be seen in Table VII, the hardness (crushing strength) of tablets containing 5% or 20% of the calcium metasilicate was similar. Replacing a portion of the DCP with calcium metasilicate did not significantly compromise the functional properties of the tablets. While an increase in the calcium metasilicate concentration of from 5 wt % to 20 wt % (accompanied by a concomitant decrease in the DCP level) increased the ejection force, the ejection force was nonetheless not raised to excessive levels. Similarly, the compactibility of DCP mixtures with calcium metasilicates declined only slightly from that of the material containing only DCP.

EXAMPLE 9

The usefulness of the calcium metasilicates prepared according to the present invention in solid compacted pharmaceutical preparations was studied making use of the calcium metasilicate prepared in Example 6. In this example, the common excipient for comparison was microcrystalline cellulose (specifically Emcocel 90M, available from Mendell-Penwest, Patterson, N.Y.). Four different tablet compositions were prepared, with one tablet composition containing no calcium metasilicate serving as a control, and another tablet containing 5 wt % fumed silica (specifically, Cab-O-Sil M5® available from the Cabot Corporation, Bellrica, Mass.) and microcrystalline cellulose for comparative purposes. In the remaining two tablet compositions contained calcium metasilicate prepared in Example 6 was substituted for the microcrystalline cellulose at levels of 5 wt % and 20 wt %. The exact compositions of the tablets are set forth below in Table VIII. The powder tablet compositions were compacted into tablets at two different compactions forces, 7.5 kN and 12 kN, on a Stokes B-2 16-station rotary press instrumented to measure compression and ejection forces. For each tablet composition, ten samples were made, the properties of each sample measured, and the average values of the measurements set forth in Table IX, below.

TABLE VIII

Tablet Compositions

|  | Tablet 4 | Tablet 5 | Tablet 6 | Tablet 7 |
|---|---|---|---|---|
| Calcium metasilicate (Example 6) | 0% | 5% | 20% | 0% |
| Microcrystalline Cellulose | 99% | 94% | 79% | 94% |
| Cab-O-Sil M5 Silica | 0% | 0% | 0% | 5% |
| Magnesium stearate | 1% | 1% | 1% | 1% |
| Total tablet weight, mg | 330 | 315 | 320 | 290 |

TABLE IX

Functional Tablet Properties

| | 7.5 KN Compression Force | | 12 KN Compression Force | |
|---|---|---|---|---|
| | Hardness (Kpa) | Ejection Force (kg) | Hardness (Kpa) | Ejection Force (kg) |
| Tablet 4 | 13.2 | 1.3 | Capping | 1.4 |
| Tablet 5 | 15.4 | 2.1 | 22.5 | 2.2 |
| Tablet 6 | 15.8 | 4.3 | 23.8 | 4.6 |
| Tablet 7 | Not tested | Not tested | 18.8 | 6.1 |

From Table IX, it may be seen that the hardness or crushing strength of tablets containing 5% or 20% of the calcium metasilicate of example 6 was similar. While an increase of from 5% to 20% metasilicate increased the ejection force, the ejection force was not excessive.

One especially interesting phenomenon was observed. It can be seen in Table IX that the microcrystalline cellulose control, Tablet 4, with the same 1% magnesium stearate did not make successful tablets when compressed to 12 kN. The control (Tablet 4, containing only microcrystalline cellulose and no calcium metasilicate) did not make successful tablets when compressed to 12 kN due to capping (when the tablet delaminates during or following discharge from the tablet press). However, when the tablet composition included 5% or 20% of the calcium metasilicate of Example 6 (tablet 5 and tablet 6, respectively), capping was eliminated and tablet crushing strengths were very high for typical tablets, reaching in excess of 20 kPa at 12 KN compression force.

These results suggest that the compacted calcium metasilicate has the ability to provide a measure of protection to microcrystalline cellulose ("MCC") from the deleterious effects of magnesium stearate. It is well-known that magnesium stearate can substantially reduce the compactibility of MCC. This is usually not a serious concern, because the compactibility of MCC is so high that a loss of crushing strength caused by magnesium stearate does not typically affect the performance of compositions incorporating both magnesium stearate and MCC. However, when added at relatively high concentrations and compressed with sufficient force, tablets containing MCC and magnesium stearate can show capping, and in fact, this system has been used as a model "capping" system in pharmaceutical tablet research.

Previously, it has been noted that fumed silicas offer a similar protective effect against the "softening" of MCC-containing tablets caused by the "over-mixing" of magnesium stearate into the tablet compositions. It is believed that the softening observed in over-mixing results when the over-mixing causes the magnesium stearate to delaminate to produce excess particles in the mix that excessively coat the filler surfaces.

An explanation for the protective effects provided by fumed silica (and in the present case, calcium metasilicate) against tablet softening has not been well-researched, but in the case of fumed silica, is believed to be the result of fumed silica interacting with free magnesium stearate particles. In the present example, the protective effect of 5% Cab-O-Sil silica has been confirmed. However, what has also been determined is that, when incorporated in a tablet composition, the calcium metasilicates prepared according to Example 6 offer much better protection against tablet softening than the fumed silica materials. As can be seen from Table IX, tablets incorporating the calcium metasilicate prepared according to the present invention (5 wt % of Example 6 calcium metasilicate) had greater crushing strengths than conventional tablet compositions containing fumed silica (5 wt % Cab-O-Sil silica). Additionally, the ejection force of the tablet composition including Example 6 calcium metasilicate was significantly lower than the ejection force of the tablet composition containing Cab-O-Sil fumed silica.

EXAMPLE 10

As a further test of the tableting performance of calcium metasilicate prepared according to the present invention, the compactibility of tablets containing calcium metasilicates prepared according to the present invention was compared to tablets containing standard excipients, such as microcrystalline cellulose and dicalcium phosphate dihydrate, by Heckel analysis.

Heckel analysis is a method of describing and determining important properties of pharmaceutical powders and tablets, such as yield strength. Heckel analysis is discussed in greater detail in R. W. Heckel, 221 Trans. Metall. Soc. A.I.M.E. 671 (1961), and R. W. Heckel, 221 Trans. Metall. Soc. A.I.M.E. 1001 (1961).

A pellet press, such as a Colton 321 single station press, that is instrumented to measure compressive forces is used for the Heckel analysis. During powder compression, particles undergo elastic deformation, which tends to lower the porosity of the powder bed. Heckel analysis analyzes the effects of elastic deformation on the calculation of porosity of a tablet. The effects of a small change in porosity, indicated by changes in density, on Heckel analysis are presented mathematically, in Equation 2:

$$Ln[1/(1-D)] = KP + A \quad \text{(Equation 2)}$$

where D=Compressed density/ True density;

P is the applied compression pressure;

and A is a constant related to densification due to particle rearrangement.

In the present case compacts having an 8.8 mm diameter were prepared at compression forces from 200±20 MPa. The Heckel plots were constructed by plotting the natural log of the inverse of the compact porosity against the respective compression pressures. The regression analysis was performed on the linear portion of the curve. The slope values obtained (K) were converted to mean deformation yield pressures ($P_y$) using the relationship of Equation 3:

$$P_y = 1/K \quad \text{(Equation 3)}$$

Elastic deformation causes positive deviations in the Heckel plot, and therefore leads to a yield strength that is lower than the true value. The lower the elastic modulus of the powder, the greater is the deviation from the true value. Low values of Py describe powders that are ductile in nature, whereas, high $P_y$ values describe powders comprised of brittle particles. The area under the Heckel curve is used to express the extent of volume reduction (i.e., compressibility) that the material had undergone during the entire compression pressure range.

Separate tablets were prepared using the calcium metasilicates prepared in Examples 4–6. Also separately prepared were two control tablets containing the conventional excipients DCP and microcrystalline cellulose. All tablets were prepared neat. Preliminary to the Heckel analysis, it is necessary to know the true densities of the materials to be evaluated. For each tablet powder and excipient, specimen samples were made, the true densities for 3–9 specimens of each tablet powder was measured using Micromeritics multivolume pycnometer Model 1305, and the measured true density values averaged. The average true density results are set forth in Table X, below.

TABLE X

True Density and Heckel Parameters

| Excipient in Tablet | Average Crushing Force, kP | True Density g/cc | K $Mpa^{-1}$ | A | $P_y$ Mpa |
|---|---|---|---|---|---|
| Emcompress DCP | 5.7 | 2.297 | 0.0045 | 1.033 | 225 |
| Emcocel 90M MCC | max off scale | 1.549 | 0.0116 | 0.827 | 87 |
| Example 4 | 3.6 | 2.774 | 0.0020 | 0.481 | 505 |
| Example 5 | 15.9 | 1.711 | 0.0044 | 0.358 | 229 |
| Example 6 | 19.6 | 1.865 | 0.0032 | 0.339 | 316 |

It is widely-known in the pharmaceutical industry that microcrystalline cellulose is the most compactible excipient available for solid dosage forms. But as can be seen in Table X, the tablets prepared using Example 5 and 6 calcium metasilicates have crushing forces far exceeding of the control tablet prepared with dicalcium phosphate. Such greatly improved performance would not have been expected by one of ordinary skill in the art.

EXAMPLE 11

In this example, calcium metasilicates prepared according to Example 4 were used in tablets in combination with other common excipients and disintegrants to promote rapid tablet disintegration. 500 mg tablets were made by direct compression in an Angstrom pellet press at 1.3 kN. The mould had a circular shape and a diameter of 1.4 cm. The tablet compositions are set forth below, in Table XI. A common aspirin tablet was included in the disintegration tests for comparative purposes. The tablets were immersed in deionized water at 37° C. and the time required for initial fracture of the tablet as well as the dynamics of the disintegration is set forth below in Table XI.

TABLE XI

Tablet Properties

| Excipient or Disintegrant | wt % of Excipient or Disintegrant | wt % Example 4 product | Initial Tablet Fracture Time, seconds | Disintegration Dynamics |
|---|---|---|---|---|
| Nymcel ZSX | 60 | 40 | >60 | Swell |
| Super-Tab | 60 | 40 | 18 | Fracture/disintegrate |
| Ac-Di-Sol | 60 | 40 | 15/17 | Swell/rupture |
| Satialgine H8 | 60 | 40 | 5/8 | Swell/split |
| Amberlite IRP 88 | 60 | 40 | 12 | Breakaway from surface |
| Explotab | 60 | 40 | 18 | Swell/split |
| Aspirin Tablet | — | — | 72 | Slight swelling, fracture |

The Aspirin Tablets used were over-the-counter 325 mg dosage from Bayer Corporation, Morriston, N.J. Explotab® is NF grade Sodium Starch Glycolate available from Penwest Pharmaceuticals, Patterson, N.Y., and Satialgine H8 is NF grade alginic acid also available from Penwest Pharmaceuticals. Amberlite® IRP 88 is NF grade polyacriline potassium from Rohm and Haas, Philadelphia, Pa. Nymcel® ZSX is NF grade microcrystalline cellulose from Noviant Ltd., Nijmegen, NL. Super-Tab® is NP grade spray dried lactose monohydrate from FMC, Inc., Philadelphia, Pa., and Ac-Di-Sol® is NF grade Croscarmellose Sodium also available from FMC, Inc.

As can be seen in the table, when the calcium metasilicate of the present invention was used in combination with several commonly used disintegrants, the result was a rapidly disintegrating tablet. The calcium silicate was effective regardless of the mechanism employed by the disintegrant, and in all but one case the tablets disintegrated in less than 20 seconds. Such significant improved disintegration performance would not have been expected by one of ordinary skill in the art.

EXAMPLE 12

A series of tablet compositions (made according to the formulas set forth in Table XII below) were pressed into tablets over a range of direct compression pressures (see Table XIII). Excipient grade fillers and disintegrants were combined with DCP, MCC or the calcium metasilicate prepared in Example 4 to form a homogenous mixture. Thereafter magnesium stearate lubricant was added to the mixture and blending was continued for an additional 3 minutes. For each mixture, 500 mg tablets were made by direct compression in an Angstrom pellet press at forces of 3.6, 4.4, and 8.9 kN. The Angstrom press mould had a circular shape and a diameter of 1.4 cm. The compositions of each tablet are set forth below in Table XII, below as formulas 1–5. Each tablet contained the same relative amount of excipient, disintegrant, filler and lubricant, but the specific excipient, disintegrant, and filler used in each tablet varied as set forth below in Table XII. The same lubricant, magnesium stearate, was used in the same concentration in all five formulas. The tablets were immersed in deionized water at 37° C. and the time required for initial fracture of the tablet as well as the dynamics of the disintegration is set forth below in Table XIII.

TABLE XII

Tablet Compositions

| Component, wt % | Formula 1 | Formula 2 | Formula 3 | Formula 4 | Formula 5 |
|---|---|---|---|---|---|
| Excipient, 40% | MCC | Example 4 | DCP | Example 4 | Example 4 |
| Disintegrant, 10% | Explotab | Ac-Di-Sol | Explotab | Explotab | Explotab |
| Filler, 49% | Sucrose | Sucrose | Sucrose | Lactose monohydrate | Sucrose |
| Lubricant, 1% | Magnesium stearate | Magnesium stearate | Magnesium stearate | Magnesium stearate | Magnesium stearate |
| Tablet weight, mg | 500 | 500 | 500 | 500 | 500 |

DCP is Dibasic Calcium Phosphate available from Rhodia Corporation, Cranbury, N.J. MCC is Microcrystalline Cellulose available from Mendell-Penwest, Patterson, N.Y.

TABLE XIII

Disintegration rate for the tablets prepared according to Example 12 with Different Excipients and Compression Forces

| | | Formula 1 | Formula 2 | Formula 3 | Formula 4 | Formula 5 |
|---|---|---|---|---|---|---|
| Primary Excipient | | MCC | Example 4 | DCP | Example 4 | Example 4 |
| Compression Force | 3.6 KN | 4 | 11 | Not compressible | 7 | 15 |
| | 4.4 KN | >300 | 10 | 13 | 5 | 12 |
| | 8.6 KN | >300 | 27 | >120 | 6 | 49 |

The numbers given in the table, above, indicate the amount of time (in seconds) for the tablets to visually reach a point of essentially complete disintegration.

These tests show that the calcium metasilicate of this invention allows the drug formulator to design a rapidly disintegrating tablet that combines excellent tablet integrity and quick disintegration times when used in combination with other common excipients, disintegrants and fillers.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A calcium metasilicate having an aspect ratio (average major axial diameter/average minor axial diameter) of from about 1:1 to about 2.5:1, and an oil absorption of from about 20 ml/100 g to about 220 ml/100 g.

2. The calcium metasilicate according to claim 1, wherein the calcium metasilicate has a CaO/SiO$_2$ molar ratio of 0.75 to 1.3.

3. The calcium metasilicate according to claim 1, wherein the calcium metasilicate has a CaO/SiO$_2$ molar ratio of 0.95 to 1.05.

4. The calcium metasilicate according to claim 1, wherein the calcium metasilicate is dehydrated.

5. The calcium metasilicate according to claim 1, wherein the calcium metasilicate is calcined.

6. The calcium metasilicate according to claim 1, wherein the calcium metasilicate is wollastonite.

7. The calcined calcium metasilicate according to claim 1, wherein the calcium metasilicate is wollastonite having a monoclinic crystal habit.

8. The calcium metasilicate of claim 1, wherein the calcium metasilicate contains less than 0.5% crystalline silica.

9. The calcium metasilicate of claim 1, wherein the calcium metasilicate is amorphous.

10. A veterinary pharmaceutical preparation comprising the calcium metasilicate of claim 1.

11. A formed food product comprising the calcium metasilicate of claim 1.

12. A formed agricultural product comprising the calcium metasilicate of claim 1.

13. A formed home care product comprising the calcium metasilicate of claim 1.

14. A method of forming the calcium metasilicate of claim 1 in dehydrated form, comprising the steps of:
   (a) providing a calcium source and a silica source, wherein a molar ratio of calcium in the calcium source to silica in the silica source is from about 0.75 to about 1.3;
   (b) mixing the calcium source with the silica source to form a homogeneous mixture; and
   (c) heating the homogenous mixture to form the dehydrated calcium metasilicate.

15. The method according to claim 14, wherein the calcium source is selected from the group consisting of calcium oxide, calcium hydroxide, calcium silicate, calcium chloride, and the silica source is selected from the group consisting of synthetic silica and naturally occurring silica.

16. The method according to claim 15, wherein the synthetic silica is selected from the group consisting of fumed silica, silica gels, precipitated silica, silica sols, and silicic acid.

17. The method according to claim 14, wherein water is provided in step (a) so that the homogeneous mixture is in the form of a suspension.

18. The method according to claim 14, wherein following step (b), the method further comprises the step of (b') drying the suspension.

19. The method according to claim 14, wherein in step (c) the dehydrating occurs at a temperature of between about 600° C. and 1200° C.

20. The method according to claim 14, wherein the dehydrating in step (c) is a calcining process.

21. The method according to claim 14, including dehydrating the homogeneous mixture for about 10 minutes to about 120 minutes.

22. A formed pharmaceutical product comprising:
(a) a pharmaceutically active ingredient; and
(b) a calcium metasilicate excipient having an aspect ratio (average major axial diameter/average minor axial diameter) of from about 1:1 to about 2.5:1, and an oil absorption of from about 20 ml/100 g to about 220 ml/100 g.

23. The formed pharmaceutical product of claim 22, wherein the pharmaceutical product is in tablet form.

24. The formed pharmaceutical product of claim 22, wherein the pharmaceutical product is in granular form.

25. The formed pharmaceutical product according to claim 22, further comprising a disintegrant selected from the group comprising starch, modified starch, pregelatinized starch, cellulose, chemically-modified cellulose, gums, agar gum, guar gum, locust bean gum, karaya gum, pectin gum, tragacanth gum, alginic acid, salts of alginic acid, acetates, citrates, sugars, aluminium oxide, crospovidone, croscarmellose, and effervescent disintegrants.

26. The formed pharmaceutical product according to claim 22, further comprising a disintegrant selected from the group comprising starch, modified starch, pregelatinized starch, cellulose, chemically-modified cellulose, gums, agar gum, guar gum, locust bean gum, karaya gum, pectin gum, tragacanth gum, alginic acid, salts of alginic acid, acetates, citrates, sugars, aluminium oxide, crospovidone, croscarmellose, and effervescent disintegrants.

27. A cosmetic product comprising:
(a) one or more cosmetic ingredients; and
(b) a dehydrated calcium metasilicate excipient having an aspect ratio (average major axial diameter/average minor axial diameter) of from about 1:1 to about 2.5:1, and an oil absorption of from about 20 ml/100 g to about 220 ml/100 g.

28. A formed product comprising:
(a) a disintegrant; and
(b) a dehydrated calcium metasilicate excipient having an aspect ratio (average major axial diameter/average minor axial diameter) of from about 1:1 to about 2.5:1, and an oil absorption of from about 20 ml/100 g to about 220 ml/100 g;
wherein the formed product disintegrates in less than about 30 seconds when immersed in water at 37° C.

* * * * *